United States Patent [19]

Röchling et al.

[11] Patent Number: 5,364,832
[45] Date of Patent: Nov. 15, 1994

[54] WATER-DISPERSIBLE GRANULES COMPRISING FENOXAPROP-ETHYL AND/OR FENCHLORAZOLE

[75] Inventors: Hans Röchling, Bad Soden am Taunus; Jean Kocur, Hofheim am Taunus; Konrad Albrecht, Kelkheim/Taunus, all of Germany

[73] Assignee: Hoechst Aktiengesellschaft, Frankfurt am Main, Germany

[21] Appl. No.: 884,701

[22] Filed: May 18, 1992

Related U.S. Application Data

[63] Continuation of Ser. No. 565,666, Aug. 10, 1990, abandoned.

[51] Int. Cl.$^5$ ............ A01N 25/32; A01N 43/76; A01N 43/653
[52] U.S. Cl. ............ 504/272; 504/106; 504/270; 71/DIG. 1
[58] Field of Search ............ 504/106, 270, 272

[56] References Cited

U.S. PATENT DOCUMENTS

| | | | |
|---|---|---|---|
| 3,920,442 | 11/1975 | Albert et al. | 71/92 |
| 4,668,276 | 5/1987 | Handte et al. | 71/88 |
| 4,936,901 | 6/1990 | Surgant, Sr. et al. | 71/92 |

FOREIGN PATENT DOCUMENTS

| | | |
|---|---|---|
| 0036106 | 2/1981 | European Pat. Off. . |
| 0026918 | 4/1981 | European Pat. Off. . |
| 0141436 | 5/1985 | European Pat. Off. . |
| 0141437 | 5/1985 | European Pat. Off. . |
| 0135963 | 6/1985 | European Pat. Off. . |
| 0174562 | 3/1986 | European Pat. Off. . |
| 0224845 | 6/1987 | European Pat. Off. . |
| 0255760 | 2/1988 | European Pat. Off. . |
| 1373296 | 8/1964 | France . |
| 3909455 | 9/1990 | Germany . |
| 1401304 | 7/1975 | United Kingdom . |

OTHER PUBLICATIONS

Niitechem 1988, p. 1.
H. B. Ries et al., Granuliertechnik und Granuliergeräte, Aufbereitungs-Technik, Nr. 3, (1970), pp. 147 to 153.
Michael Rosch et al., Granulation in der Wirbelschicht, Verfahrenstechnik, vol. 9, Nr. 2, (1975), pp. 59 to 64.

*Primary Examiner*—Glennon H. Hollrah
*Assistant Examiner*—S. Mark Clardy
*Attorney, Agent, or Firm*—Curtis, Morris & Safford

[57] ABSTRACT

Novel water-dispersible granules of plant protection agents, in particular of herbicides and growth regulators, are obtained when a dispersion or solution in water of 10 to 90% by weight of active substance with 10 to 90% by weight of solid wetting agents from the group containing of alkanesulfonates, alkylsulfonates, alkylnaphthalenesulfonates, alkylbenzenesulfonates, long-chain olefinsulfonates, alkyl polyol ether sulfonates, alkyl ether sulfates, alkyl ether phosphates, alkylsulfosuccinic monoesters, fatty acid isethionates and fatty acid N-methyltaurides, or of an ammonium salt, or of a mixture of an ammonium salt and one or more of the above solid wetting agents, and 0 to 50% by weight of customary formulation agents is prepared and the dispersion or solution is granulated using the cocurrent or counter-current process.

1 Claim, No Drawings

WATER-DISPERSIBLE GRANULES COMPRISING FENOXAPROP-ETHYL AND/OR FENCHLORAZOLE

This application is a continuation of Ser. No. 07/565,666, filed Aug. 10, 1990, now abandoned.

The present invention relates to novel water-dispersible granules for use in plant protection.

Plant protection agents are commercially available, mainly in the form of wettable powders, emulsifiable concentrates or aqueous dispersions. To prepare spray liquors, the agents are stirred into water.

Handling these presentation forms is not without problems. For example, the preparation and use of formulations of wettable powders often involve the occurrence of troublesome dust.

Emulsifiable concentrates contain solvents which may be readily inflammable, may irritate the skin or may cause troublesome odors.

Dispersions may form sediments upon long storage which can be difficult to shake up. Moreover, there are often problems in this type of formulation as regards the disposal of the packaging materials.

The water-dispersible granules (abbreviated "WG") do not have these disadvantages since they are free-flowing, low in dust and can be readily metered out. They can be packaged without problems in polyethylene containers, gusseted bags made of laminated film (paper/aluminum/plastic) or cardboard boxes, all of which can be disposed of readily.

A large number of processes are available for the industrial preparation of dispersible granules (cf. H. B. Ries "Granuliertechnik und Granuliergeräte [Granulation Technology and Granulation Apparatuses]" in Aufbereitungstechnik No. 3, 1970, p. 147 and M. Rosch and R. Probst in Verfahrenstechnik 9 (1975) p. 59 to 64).

In particular, it is known to prepare water-dispersible granules using the fluidized-bed process which can be carried out in countercurrent and in cocurrent.

U.S. Pat. No. 3,920,442 and GB-A 1,401,304 as well as M. Rosch and R. Probst in Verfahrenstechnik 9 (1975) p. 59 describe the countercurrent process, while the cocurrent process is described in EP-A 0,026,918, EP-A-0,141,436 and EP-A 0,141,437 and also in Verfahrenstechnik 9 (1975), p. 61/62.

To guarantee perfect use, it is necessary for the water-dispersible granules to be thoroughly wetted when they are introduced into water, to disintegrate as spontaneously as possible, and to form a suspension with good suspendibility.

However, the most important prerequisite for the usability of water-dispersible granules in practice is sufficiently high biological activity. There is a series of active substances which require the addition of wetting agents to achieve their optimum biological action. Most of these wetting agents are liquid. If substantial amounts of these liquid wetting agents are used in liquid preparations such as, for example, emulsifiable concentrates, there are usually no problems. However, if this formulation type is to be replaced by a WG formulation for the abovementioned reasons which are relevant to the environment, there result considerable technical difficulties: the substantial amounts of liquid wetting agents, which are required in most cases, cannot be incorporated into the solid formulation mentioned.

Surprisingly, it has now been found that when certain solid wetting agents and/or ammonium salts are used, it is possible to prepare water-dispersible granules whose technical properties in use are perfect and whose biological actions are not reduced compared with emulsifiable concentrates and often even improved.

The invention relates to water-dispersible granules which contain a) 10 to 90% by weight, preferably 20 to 80% by weight, of one or more plant protection agents, b) 10 to 90% by weight, preferably 20 to 85% by weight, of one or more solid wetting agents from the group containing alkanesulfonates, alkyl sulfates, alkylnaphthalenesulfonates, alkylbenzenesulfonates, long-chain olefinsulfonates, alkyl polyglycol ether sulfonates, alkyl ether sulfates, alkyl ether phosphates, alkylsulfosuccinic monoesters, fatty acid isethionates and fatty acid N-methyltaurides, or of an ammonium salt, or of a mixture of an ammonium salt and one or more of the above solid wetting agents, and c) 0 to 50% by weight, preferably 0 to 15% by weight, of customary formulation agents, in particular from the group of the inert substances, fillers, dispersants, binders, wetting agents, penetrants, tackifiers, adhesives and antifoam agents.

Examples of active substances in which larger amounts of wetting agents in the formulations may be advantageous to increase their biological activity include the group of the herbicides and growth regulators, such as, for example, glufosinate-ammonium(D,L-phosphinothricin-ammonium), L-phosphinothricin-ammonium, D,L- and D-fenoxaprop-ethyl and diclofop-methyl, as well as mixtures of racemic fenoxaprop-ethyl or D-fenoxaprop-ethyl with safeners such as, for example, from the series of the 1-phenyltriazolecarboxylic esters (cf. EP-A-0,174,562, for example Examples 3 to 172 described therein, in particular fenchlorazole, ISO Document No. TC 81N 896 of the British Standard Institution), from the series of the 1-arylpyrazolecarboxylic acid derivatives (cf. European Patent Application No. 89,104,500.7, in particular Examples 1 to 1236 therein), or from the series of the pyridazinone derivatives (cf. European Patent Application No. 89,109,649, Examples 1 to 222); furthermore mixtures of D,L- or D-fenoxaprop-ethyl with sulfonylureas such as the N-alkoxy- and N-alkylsulfonylaminosulfonylureas disclosed in EP-A 013,258, for example Hoe 75032 or other sulfonylureas such as DPX T 6376 (Ally ®, Gropper ®), DPX-L 5300 (Granstar ®) and DPX M 6316 (Harmony ®) and the like, and also mixtures of D,L- or D-fenoxaprop-ethyl with the abovementioned safeners and the sulfonylureas mentioned; mixtures of D,L- or L-glufosinate-ammonium with other herbicides such as, for example, diuron, linuron, monolinuron, aminotriazole, imazapyr, oxyfluorfen, simazine, diuron + simazine, and with sulfonylureas such as, for example, Hoe 75032, DPX T 6376 (Ally ®), Gropper ®), DPX L 5300 (Granstar ®) and DPX M 6316 (Harmony ®), are also included.

The active substances mentioned are known and described in the publications mentioned or, most often, in "The Pesticide Manual", 8th edition, British Crop Protection Council, 1987. DPX-T 6376, DPX-L 5300 and DPX-M 6319 are commercially available herbicides manufactured by DuPont and described in "Farm Chemicals Handbook '89" (Meister Publishing Company, Willoughby, Ohio, 1989).

Examples of suitable solid wetting agents in the water-dispersible granules according to the invention are:

sodium lauryl sulfate (for example ®Texapon K12 or Texapon Z), sodium alkylnaphthalenesulfonates (for example ®Supragil WP), alkylnaphthalenesulfonates (for example ®Sellogen DFL), sodium oleoylmethyltauride (for example ®Hostapon T), sodium dibutylnaphthalenesulfonate (for example ®Leonil DB), sodium dodecylbenzenesulfonate (for example ®Phenylsulfonate HS 90, ®Ufaryl DL 85 or ®Nansa HS 80), di-sodium salt of iso-decylsulfosuccinic monoester (for example Netzer IS), sodium lauryl ether phosphate (for example ®Forlanit P), sodium $C_{14}$-$C_{19}$-olefinsulfonate (for example ®Hostapur OS), secondary n-alkanesulfonate (for example ®Hostapur SAS), sodium alkyldiglycol ether sulfate (for example ®Genapol LRO). The wetting agents mentioned are commercially available.

The invention also relates to a process for preparing the water-dispersible granules according to the invention, which process comprises preparing a dispersion or solution of the, or of some of the, components a), b) and c), or of part of the components, in water, and granulating the dispersion or solution using the countercurrent or cocurrent process, if appropriate with the addition or initial introduction of further customary granulation auxiliaries and of the remaining components. The water-dispersible granules according to the invention can be obtained analogously to the general processes for preparing granules mentioned at the outset. It is preferred to prepare the water-dispersible granules from solutions or dispersions by fluidized-bed granulation as described in EP-A 0,224,845 and German Patent 3,909,455.3.

As regards the use of combinations of wetting agents and ammonium salts, it has been disclosed that the biological activity of D,L- or L-glufosinate-ammonium can be enhanced by adding inorganic or organic ammonium salts such as, for example, ammonium sulfate, but also by urea (cf. EP 0,036,106); however, only a limited addition of ammonium salts is possible in the case of liquid formulations of the active substances mentioned, because of the solubility properties of glufosinate-ammonium and ammonium sulfate. In the case of the granules according to the invention, in particular those with D,L- and L-glufosinate-ammonium as well as the mixtures of the two active substances with diuron, linuron, monolinuron, aminotriazole, oxyfluorfen, simazine, diuron+ simazine and the sulfonylureas Hoe 75032, DPX T 6376, DPX L 5300 and DPX M 6316, it is possible, surprisingly, to replace the solid wetting agents completely or partially by ammonium salts such as, in particular, by ammonium sulfate, i.e., it is possible to prepare granules with good technical properties in use, in particular also granules having high salt contents. As component (b), the water-dispersible granules according to the invention preferably contain one or more of the solid wetting agents or a mixture of an ammonium salt with one or more of the solid wetting agents, the ratio by weight of ammonium salt: wetting agent being up to 1.5:1, in particular up to 1:1.

It is surprising that by partially replacing the solid wetting agents by ammonium salts such as, for example, inorganic ammonium salts, in particular ammonium sulfate, the same biological activity can be obtained, as is achieved in the corresponding formulation without ammonium salts. Such a replacement of solid wetting agent by ammonium salts can have considerable price advantages since ammonium salts such as, for example, ammonium sulfate, are considerably more inexpensive than solid wetting agents.

The invention also relates to the use of the water-dispersible granules according to the invention as plant protection agents, in particular as herbicidal agents. The application rate depends on the particular active substance employed and can vary within broad limits; for example, in the case of herbicides, generally between 0.005 and 10 kg/ha of active ingredient.

When used, the granules according to the invention are processed with water (diluted) to give a spray liquor, analogously to wettable powders and liquid formulations, and they are applied to the plants or the areas under cultivation in this form. Apart from being metered out more easily and having better storability and other technical properties in use such as, for example, a better possibility for packaging, the active substances formulated in this manner have a very good biological activity which generally corresponds to the biological activity of liquid formulations or even surpasses the latter.

A. Preparation Examples

General information on assessment and preparation

The spontaneous dispersibility of the granule formulation is assessed using a scale from 1 to 4. For this purpose, 1 g of the granules is first transferred into a 1 l measuring cylinder which is filled with standardized water (30° C., 342 ppm, $CaCo_3$ water hardness). After 1 minute, the measuring cylinder is slowly turned by 180° C. and then returned to the initial position. This procedure is repeated three times. For the assessment, the scheme below is used.

Scale

1 All individual granules are dispersed.
  If there are any undispersed granule particles, the cylinder is shaken another three times as described 2 minutes after commencement of the test and assessed as follows:
2 The granules are now completely dispersed.
3 Residual granules are not dispersed.
4 Most of the granules are not dispersed.

The suspendibility was indicated as the amount of the preparation (% by weight) which is located in the upper nine tenths parts by volume of a suspension after a sedimentation time of 30 minutes has elapsed (see CIPAC-Handbook Vol. 1 (1970), p. 861).

The wet-screening residue is understood as meaning the amount of substance which remains on a screen of 250 µm or 71 µm after rinsing for 10 minutes with a defined amount of water. A description of the method can be found in "Specification for pesticides used in public health", WHO Geneva, p. 281 (1973).

A laboratory spray dryer (Büchi 190 (Büchi Laboratoriumstechnik GmbH, P.O. Box 11 54, 7332 Eislingen/Fils) is used for spray-drying smallish amounts, and a laboratory fluidized-bed granulator Büchi 710 is employed for fluidized-bed granulation.

For batches of up to 400 g of product, a laboratory fluidized-bed "Combi Coater" manufactured by Niro-Atomizer was used. Larger batches of up to 15 kg of product were carried out on a fluidized bed manufactured by Glatt (GPCG 5).

EXAMPLE 1 a) Dispersion for preparing the granules 111 g of a dispersion of the following composition are prepared:

9.30% by weight of D,L-fenoxaprop-ethyl, technical grade, 96.8%
33.45% by weight of Na $C_{14}$–$C_{19}$-olefinsulfonate (®Hostapur OS)
0.90% by weight of defoamer SE 2 (defoamer based on silicone)
1.35% by weight of a cresol/formaldehyde condensation product (dispersant Hoe S 1494)
55.00% by weight of drinking water For this purpose, the components are mixed and the mixture is ground with the aid of a bead mill until 50% of the particles have a size of 2–3 μm.

b) Preparation of the granules

Approximately one third of the dispersion prepared under a) is spray-dried. The resulting fine powder is initially placed in a laboratory fluidized-bed granulator and granulated by spraying on the remainder of the dispersion.

Dry gas temperature: 50°–60° C.

In this manner, water-dispersible granules of the following composition are obtained:
20.66% by weight of D,L-fenoxaprop-ethyl, technical grade, 96.8%
74.34% by weight of Na $C_{14}$–$C_{19}$-olefinsulfonate (®Hostapur OS)
2.00% by weight of defoamer SE 2
3.00% by weight of dispersant based on a cresol/formaldehyde condensation product (dispersant Hoe S 1494)
Yield: 90.5%
Particle size 0.8 to 1.2 mm (granules):
Spontaneous dispersibility: 1
Suspendibility: 88%

EXAMPLE 2 a) Dispersion 210 g of a dispersion of the following composition are prepared:
4.96% by weight of D,L-fenoxaprop-ethyl, technical grade, 96.8%
10.80% by weight of Na alkyl diglycol ether sulfate (®Genapol LRO)
0.24% by weight of defoamer on silicone base (defoamer SE 2)
0.72% by weight of dispersant based on a cresol/formaldehyde condensation product (dispersant Hoe S 1494)
7.28% by weight of aluminum silicate (Perlite I-206, ground obsidian rock)
76.00% by weight of drinking water The components are mixed and the mixture is ground with the aid of a bead mill until 50% of the particles have a size of 2–3 μm.

b) Granules

Approximately one third of the dispersion prepared under a) is spray-dried. The resulting fine powder is initially placed in a laboratory fluidized-bed granulator and granulated by spraying on the remainder of the dispersion at a dry gas temperature of 55°–65° C.

Granules of the following composition are obtained:
20.66% by weight of D,L-fenoxaprop-ethyl, technical grade, 96.8%
45.00% by weight of ®Genapol LRO
1.00% by weight of defoamer SE 2
3.00% by weight of dispersant Hoe S 1494
30.34% by weight of ®Perlite I-206
Yield: 73.3%
Particle size 0.8 to 1.3 mm (granules):
Spontaneous dispersibility: 1
Suspendibility: 85%

EXAMPLE 3

Analogously to Examples 1 and 2, granules of the following composition are prepared:
0.31% by weight of D-fenoxaprop-ethyl, 97%
5.00% by weight of Genapol LRO
1.00% by weight of defoamer SE 2
3.00% by weight of dispersant Hoe S 1494
40.69% by weight of ®Perlite I-206
Yield: 73.2%
Particle size 0.7 to 1.2 mm (granules):
Spontaneous dispersibility: 1
Suspendibility: 86%

EXAMPLE 4

Analogously to Examples 1 and 2, granules of the following composition are prepared:
10.31% by weight of D-fenoxaprop-ethyl, 97%
46.00% by weight of ®Hostapur OS
1.00% by weight of defoamer SE 2
4.00% by weight of dispersant Hoe S 1494
38.69% by weight of ®Perlite I-206
Yield: 87.2%
Particle size 0.4 to 1.5 mm (granules):
Spontaneous dispersibility: 1
Suspendibility: 92%

EXAMPLE 5

Granules of the following composition are prepared as described in Examples 1 and 2:
0.31% by weight of D-fenoxaprop-ethyl, 97%
1.00% by weight of ®Hostapur OS
45.00% ght of secondary alkanesulfonate (®Hostapur SAS)
1.00% by weight of defoamer SE 2
4.00% by weight of dispersant Hoe S 1494
38.69% by weight of ®Perlite I-206
Yield: 81.4%
Particle size 0.5 to 1.1 mm (granules):
Spontaneous dispersibility: 2
Suspendibility: 82%

EXAMPLE 6

Granules of the following composition are prepared analogously to Examples 1 and 2:
10.31% by weight of D-fenoxaprop-ethyl, 97%
1.00% by weight of ®Hostapur OS
45.00% by weight of ®Ufaryl DL-85 (sodium dodecylsulfonate)
1.00% by weight of defoamer SE 2
4.00% by weight of Hoe S 1494
38.69% by weight of ®Perlite I-206
Yield: 74.2%
Particle size 0.4 to 0.9 mm (granules):
Spontaneous dispersibility: 1
Suspendibility: 79%

EXAMPLE 7

Granules of the following composition are prepared analogously to Examples 1 and 2:
10.31% by weight of D-fenoxaprop-ethyl, 97%
5.06% by weight of safener fenchlorazole, 98.9%
46.00% by weight of ®Hostapur OS
1.00% by weight of defoamer SE 2
4.00% by weight of dispersant Hoe S 1494

33.63% by weight of Perlite 1-206
Yield: 78.8%
Particle size 0.5 to 1.2 mm (granules):
Spontaneous dispersibility: 1
Suspendibility: 88%

EXAMPLE 8

Granules of the following composition are prepared analogously to Examples 1 and 2:
10.31% by weight of D-fenoxaprop-ethyl, 97%
5.06% by weight of safener fenchlorazole, 98.8%
1.00% by weight of ®Hostapur OS
45.00% by weight of ®Hostapur SAS
1.00% by weight of defoamer SE 2
4.00% by weight of Hoe S 1494
33.63% by weight of ®Perlite I-206
Yield: 81.7%
Particle size 0.3 to 0.8 mm (granules):
Spontaneous dispersibility: 1
Suspendibility: 91%

EXAMPLE 9

Granules of the following composition are prepared analogously to Examples 1 and 2:
10.31% by weight of D-fenoxaprop-ethyl, 97%
5.06% by weight of safener fenchlorazole, 98.9%
1.00% by weight of ®Hostapur OS
45.00% by weight of ®Genapol LRO
1.00% by weight of defoamer SE 2
4.00% by weight of dispersant Hoe S 1494
33.63% by weight of ®Perlite I-206
Yield: 87.4%
Particle size 0.4 to 1.1 mm (granules):
Spontaneous dispersibility: 1
Suspendibility: 89%

EXAMPLE 10

Granules of the following composition are prepared analogously to Examples 1 and 2:
0.31% by weight of D-fenoxaprop-ethyl, 97%
5.06% by weight of safener fenchlorazole, 98.8%
1.00% by weight of ®Hostapur OS
5.00% by weight of ®Ufaryl DL-85
1.00% by weight of defoamer SE 2
4.00% by weight of Hoe S 1494
33.63% by weight of ®Perlite I-206
Yield: 85.2%
Particle size 0.4 to 0.9 mm (granules):
Spontaneous dispersibility: 2
Suspendibility: 83%

EXAMPLE 11

Granules of the following composition are prepared analogously to Examples 1 and 2:
12.90% by weight of D-fenoxaprop-ethyl, 93%
6.30% by weight of safener fenchlorazole, 96%
54.00% by weight of ®Hostapur OS
10.00% by weight of dispersant based on a sulfonated cresol/formaldehyde condensation product, Na salt (®Rapidamin Reserve C)
0.50% by weight of defoamer SE 2
15.30% by weight of kaolin 1777 (finely divided clay)
1.00% by weight of residual moisture
Suspendibility: 97%
Wet-screening residue on 250 μm screen: trace

EXAMPLE 12

Granules of the following composition are prepared analogously to Examples 1 and 2:
12.90% by weight of D-fenoxaprop-ethyl, 93%
6.30% by weight of safener fenchlorazole, 96%
4.90% by weight of sulfonylurea herbicide ®DPXL 5300 (®Granstar)
54.00% by weight of ®Hostapur OS
10.00% by weight of ®Rapidamin Reserve C
0.50% by weight of defoamer SE 2
10.40% by weight of kaolin 1777
1.00% by weight of residual moisture
Suspendibility: 100%, no wet-screening residue on 250 μm screen
Yield: 87%
Spontaneous dispersibility: 2
Suspendibility: 99.6%
Particle size: 0.3–1.1 mm

EXAMPLE 13

21.05% by weight of glufosinate-ammonium, 95%
30.00% by weight of ®Genapol LRO, dry matter
11.97% by weight of kaolin 7a (divided clay)
11.98% by weight of attacote (magnesium aluminum silicate)
5.00% by weight of dispersant Hoe S 1494
10.00% by weight of calcium acetate, dried (inert substance)
10.00% by weight of ®Sipernat 50 S (precipitated silica)

Glufosinate-ammonium, kaolin, attacote, calcium acetate and ®Sipernat are mixed and the mixture is ground in a hammer bar mill. The resulting pulverulent mixture is initially introduced into a fluidized-bed granulator and granulated by spraying on an aqueous solution of ®Genapol LRO and dispersant Hoe S 1494.
Yield: 99%
Spontaneous dispersibility: 3
Suspendibility: 99.3%
Particle size: 0.5–1.8 mm

EXAMPLE 14

20.14% by weight of glufosinate-ammonium, 99.3%
73.86% by weight of ®Hostapur OS
4.00% by weight of ®Luviskol K 30 (binder polyvinylpyrrolidone)
2.00% by weight of defoamer SE 2

Glufosinate-ammonium, ®Hostapur OS and ®Luviskol K 30 are mixed and the mixture is ground in a hammer bar mill. The resulting pulverulent mixture is initially introduced into a fluidized-bed granulator and granulated by spraying on an aqueous solution of the defoamer.
Yield: 84.8%
Spontaneous dispersibility: 1
Suspendibility: 99.5%
Particle size: 0.4–1.3 mm

EXAMPLE 15

30.21% by weight of glufosinate-ammonium, 99.3%
68.00% by weight of Hostapur OS
2.00% by weight of defoamer SE 2

The pulverulent wetting agent is initially introduced. The granules are prepared by spraying on a 50% strength solution of active substance.

EXAMPLES 16–20

In each of Examples 16–20 below, a mixture of pulverized Na $C_{14}$–$C_{19}$-olefinsulfonate (®Hostapur OS) or a mixture thereof with ammonium sulfate is initially introduced and the aqueous solution of glufosinateammonium is sprayed on to form granules.

| Example No. | 16 | 17 | 18 | 19 | 20 |
|---|---|---|---|---|---|
| Glufosinate-ammonium | 20% | 20% | 20% | 20% | 20% |
| (®)Hostapur OS | 78% | 58% | 40% | 20% | — |
| Ammonium sulfate | — | 20% | 40% | 60% | 80% |
| Defoamer SE 2 | 2% | 2% | — | — | — |

The yields are between 86 and 91%, the spontaneous dispersibility is 2, and the suspendibility in all examples is more than 99%.

EXAMPLE 21

Granules of the following composition are prepared analogously to Examples 1 and 2:
- 12.00% by weight of glufosinate-ammonium
- 18.20% by weight of diuron, 99%
- 16.00% by weight of ®Hostapur OS
- 12.00% by weight of ®Genapol LRO
- 0.50% by weight of defoamer SE 2
- 5.00% by weight of sodium ligninsulfonate, degree of sulfonation 0.17 (®Vanisperse CB)
- 35.30% by weight of kaolin 1777
- 1.00% by weight of residual moisture;
  Suspendibility: 99%, no wet-screening residue on 250 μm screen

EXAMPLE 22

Granules of the following composition are prepared analogously to Examples 1 and 2:
- 12.00% by weight of glufosinate-ammonium
- 18.20% by weight of diuron, 99%
- 28.00% by weight of ®Hostapur OS
- 5.00% by weight of ®Rapidamin Reserve C
- 0.50% by weight of defoamer SE 2
- 35.30% by weight of kaolin 1777
- 1.00% by weight of water
  Suspendibility: 95%, no wet-screening residue on 250 μm screen

EXAMPLE 23

Granules of the following composition are obtained analogously to Examples 1 and 2:
- 10.00% by weight of glufosinate-ammonium
- 16.70% by weight of linuron, 95.8%
- 25.00% by weight of ®Hostapur OS
- 5.00% by weight of ®Rapidamin Reserve C
- 0.50% by weight of defoamer SE 2
- 41.80% by weight of kaolin 1777
- 1.00% by weight of residual moisture
  Suspendibility: 97%,
  no wet-screening residue on 250 μm screen

B. Biological Examples

Seeds or rhizome pieces of monocotyledon and dicotyledon weeds, or seeds of crop plants, are placed in sandy loam soil in plastic pots, covered with soil and grown in the greenhouse under good growth conditions. Three weeks after sowing, the test plants are treated in the three-leaf stage.

The water-dispersible granules, wettable powders or aqueous solutions are sprayed onto the green parts of the plants at various dosage rates at an application rate of water of 200 to 800 l/ha (converted) and, after the test plants have stood in the greenhouse under optimum growth conditions for the period indicated, the effect of the preparations was scored visually in comparison with untreated controls.

1. Comparison between a liquid formulation of glufosinate-ammonium (SL) with two water-dispersible granules (WG) of glufosinate-ammonium as claimed in the present invention.

| | | % Effect on *Commelina communis* | | |
|---|---|---|---|---|
| Product | Application rate | 11 | 14 | 21 |
| | | days after application | | |
| Glufosinate-ammonium SL (20%) | 2 l/ha | 40 | 71 | 70 |
| | 3 l/ha | 40 | 75 | 80 |
| WG as in Example 13 | 2 kg/ha | 50 | 61 | 73 |
| | 3 kg/ha | 70 | 91 | 99 |
| WG as in Example 14 | 2 kg/ha | 50 | 58 | 55 |
| | 3 kg/ha | 60 | 88 | 97 |

SL = aqueous solution

2. Comparison of tank mixes of a liquid formulation of glufosinate-ammonium (SL) and formulations of linuron and diuron, respectively, as wettable powders, with the corresponding WG formulations.

| | Application rate | % Effect 18 days after application | | |
|---|---|---|---|---|
| Product | l or kg/ha | VF | LOM | HV |
| Tank mix Glufosinate-ammonium SL (20%) + Linuron WP (48.5%) | 0.156 + 0.11 | 42 | 47 | 0 |
| | 0.3125 + 0.21 | 50 | 85 | 38 |
| | 0.625 + 0.42 | 83 | 100 | 78 |
| | 1.25 + 0.84 | 99 | 100 | 95 |
| | 2.5 + 1.68 | 100 | 100 | 100 |
| | 5.0 + 3.37 | 100 | 100 | 100 |
| WG as in Example 23 | 0.312 | 40 | 63 | 13 |
| | 0.625 | 62 | 82 | 50 |
| | 1.25 | 85 | 100 | 77 |
| | 2.5 | 96 | 100 | 99 |
| | 5.0 | 99 | 100 | 100 |
| | 10.0 | 100 | 100 | 100 |
| Tank mix Glufosinate-ammonium SL (20%) + Diuron WP (80%) | 0.156 + 0.0586 | 33 | 58 | 32 |
| | 0.31 + 0.117 | 48 | 73 | 48 |
| | 0.625 + 0.235 | 80 | 96 | 92 |
| | 1.25 + 0.469 | 90 | 100 | 98 |
| | 2.5 + 0.938 | 100 | 100 | 100 |
| | 5.0 + 1.875 | 100 | 100 | 100 |
| WG as in Example 22 | 0.26 | 35 | 45 | 32 |
| | 0.52 | 62 | 77 | 68 |
| | 1.04 | 85 | 100 | 85 |
| | 2.08 | 93 | 100 | 100 |
| | 4.17 | 99 | 100 | 100 |
| | 8.33 | 99 | 100 | 100 |
| WG as in Example 21 | 0.26 | 43 | 33 | 28 |
| | 0.52 | 65 | 88 | 80 |
| | 1.04 | 85 | 98 | 90 |
| | 2.08 | 96 | 100 | 100 |
| | 4.17 | 99 | 100 | 100 |
| | 8.33 | 100 | 100 | 100 | l or kg/ha = l/ha in the case of SL and kg/ha in the case of WG
WP = wettable powder
SL = aqueous solution
VF = *Vicia faba* (broad bean)
LOM = *Lolium multiflorum* (ray grass)
HV = *Hordeum vulgare* (barley)

3. Comparison of glufosinate-ammonium WG formulations in which increasing amounts of wetting agent were replaced by ammonium sulfate.

| Preparation Example No. | 16 | 17 | 18 | 19 | 20 |
|---|---|---|---|---|---|
| Glufosinate-ammonium | 20% | 20% | 20% | 20% | 20% |
| Hostapur OS | 78% | 58% | 40% | 20% | — |
| Ammonium sulfate | — | 20% | 40% | 60% | 80% |
| Herbicidal action in barley | = | = | = | < | << |

The symbols denote:
= same action as glufosinate-ammonium SL (20%)
< slightly less action than glufosinate-ammonium SL (20%)
<< markedly less action than glufosinate-ammonium SL (20%)

2. Comparison of a liquid formulation (EW) of D-fenoxaprop-ethyl and a tank mix of this liquid formulation with herbicide DPX L 5300 (®Granstar) with corresponding water-dispersible granules according to the invention (WG formulations).

The formulations are applied in the post-emergence method as described above, and, after 19 days, the plants are scored in comparison with untreated plants. The results are compiled in Table 4.

The abbreviations in Table 4 denote:
EW-1 = Liquid formulation with 75 g/kg D-fenoxaprop-ethyl and 37.5 g/kg fenchlorazole
WG-11 = WG according to Preparation Example 11
WG-12 = WG according to Preparation Example 12
HV = Hordeum vulgare (barley)
ALM = Alopecurus myosuroides (blackgrass)
SIA = Sinapis arvensis (wild mustard)
VIA = Viola arvensis (field violet)
-= not tested

TABLE 4

| Product | Application rate kg/ha | % Action after 19 days in | | | |
|---|---|---|---|---|---|
| | | HV | ALM | SIA | VIA |
| EW-1 | 0.20 | 10 | 80 | 0 | — |
| | 0.40 | 20 | 85 | 0 | — |
| | 0.80 | 25 | 93 | 15 | — |
| | 1.20 | 25 | 95 | 40 | — |
| WG-11 | 0.125 | 0 | 10 | 0 | — |
| | 0.25 | 15 | 65 | 0 | — |
| | 0.50 | 30 | 75 | 20 | — |
| | 0.75 | 30 | 90 | 70 | — |
| EW-1 + DPX L 5300 | 0.2 + 0.008 | 10 | 80 | 95 | 80 |
| | 0.4 + 0.016 | 20 | 85 | 95 | 85 |
| | 0.8 + 0.032 | 30 | 95 | 95 | 88 |
| | 1.2 + 0.048 | 35 | 95 | 98 | 88 |
| WG-12 | 0.125 | 10 | 80 | 85 | 80 |
| | 0.25 | 35 | 88 | 88 | 90 |
| | 0.50 | 45 | 93 | 90 | 90 |
| | 0.75 | 45 | 95 | 95 | 90 |

We claim:
1. Water-dispersible granules comprising
   a) 10 to 90% by weight at least one plant protection agent, selected from the group consisting of fenoxaprop-ethyl, fenchlorazole, and combinations thereof,
   b) 10 to 90% by weight at least one solid wetting agent selected from the group consisting of alkanesulfonates, alkyl sulfates, alkylnaphthalenesulfonates, alkylbenzenesulfonates, long-chain olefinsulfonates, alkyl polyglycol ether sulfonates, alkyl ether sulfates, alkyl ether phosphates, alkylsulfosuccinic monoesters, fatty acid isethionates and fatty acid N-methyltaurides, or of an ammonium salt, or of a mixture of an ammonium salt and at least one of the above solid wetting agents, and
   c) 0 to 50% by weight of biologically inert customary formulation agents.

* * * * *